United States Patent [19]

Ao et al.

[11] Patent Number: 4,713,381
[45] Date of Patent: Dec. 15, 1987

[54] OXODIAZINE COMPOUNDS AND PHARMACEUTICAL COMPOSITIONS THEREOF

[75] Inventors: Hideki Ao; Minoru Obata; Tsutomu Yamanaka, all of Oita; Hiroshi Mikashima, Fukuoka, all of Japan

[73] Assignee: Yoshitomi Pharmaceutical Industries, Ltd., Osaka, Japan

[21] Appl. No.: 867,170

[22] Filed: May 27, 1986

[30] Foreign Application Priority Data

May 25, 1985 [JP] Japan .................................. 60-112715

[51] Int. Cl.$^4$ .................. A61K 31/535; A61K 31/54; C07D 487/04
[52] U.S. Cl. ..................... 514/222; 514/231; 514/234; 514/236; 514/242; 544/8; 544/68; 544/182
[58] Field of Search ................ 544/8, 68; 514/222, 514/231, 234, 236

[56] References Cited

U.S. PATENT DOCUMENTS 4,558,045 10/1985 Hargreaves et al. .............. 544/68 X
4,678,785 7/1987 Ao et al. .............................. 514/222

FOREIGN PATENT DOCUMENTS 0085227 8/1983 European Pat. Off. .
120589 10/1984 European Pat. Off. .
180158 5/1986 European Pat. Off. .

*Primary Examiner*—Richard L. Raymond
*Attorney, Agent, or Firm*—Sughrue, Mion, Zinn, Macpeak & Seas

[57] ABSTRACT

An oxodiazine compound of the formula:

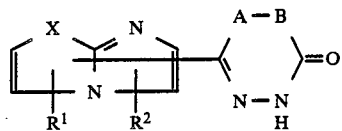

or a pharamceutically acceptable acid addition salt thereof, wherein each of $R^1$ and $R^2$ is hydrogen, halogen, $C_{1-4}$ alkyl, $C_{1-4}$ alkoxy, $C_{1-4}$ alkoxy-$C_{1-4}$ alkoxy, phenyl-$C_{1-4}$ alkyl-oxy which may be optionally substituted by at least one substituent selected from the group consisting of halogen, $C_{1-4}$ alkyl and $C_{1-4}$ alkoxy on the phenyl nucleus, or phenyl which may be substituted by at least one substituent selected from the group consisting of halogen, $C_{1-4}$ alkyl and $C_{1-4}$ alkoxy on the phenyl nucleus; X is —S—, —CH=N— or —C($R^3$)=C($R^4$)—, where each of $R^3$ and $R^4$ is hydrogen, halogen, $C_{1-4}$ alkyl, $C_{1-4}$ alkoxy, $C_{1-4}$ alkoxy-$C_{1-4}$ alkoxy or phenyl-$C_{1-4}$ alkyl-oxy which may be optionally substituted by at least one substituent selected from the group consisting of halogen, $C_{1-4}$ alkyl and $C_{1-4}$ alkoxy on the phenyl nucleus; and one of A and B is oxygen, sulfur or —NH— and the other is —C($R^5$)($R^6$)—, where each of $R^5$ and $R^6$ is hydrogen or $C_{1-4}$ alkyl.

Such compounds are useful as antithrombotic agents, antianginal agents, coronary circulation improving agent, cerebral circulation improving agents, peripheral circulation improving agents, analgesics and antiinflammatory agents.

7 Claims, No Drawings

OXODIAZINE COMPOUNDS AND PHARMACEUTICAL COMPOSITIONS THEREOF

BACKGROUND OF THE INVENTION

1. Field of the Invention

The present invention relates to novel and therapeutically valuable oxodiazine compounds, methods of preparing said compounds and a pharmaceutical composition comprising at least one of said compounds.

2. Description of the Prior Art

Antihypertensive and/or cardiotonic heterocyclic compounds inclusive of 5-(4-pyridyl)-3H,6H-1,3,4-thiadiazin-2-one are disclosed in European Patent Application No.85227.

SUMMARY OF THE INVENTION

As a result of intensive investigations to develop therapeutically useful compounds, the present inventors have found that novel oxodiazine compounds and pharmaceutically acceptable acid addition salts thereof exhibit potent inhibitory activity on platelet aggregation, increasing activity of blood flow, and analgesic and antiinflammatory activities.

DETAILED DESCRIPTION OF THE INVENTION

The oxodiazine compounds of the present invention are represented by the following formula:

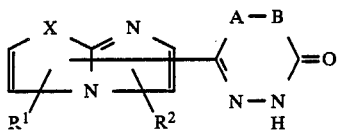
(I)

In the above formula, each of $R^1$ and $R^2$ is hydrogen, halogen, $C_{1-4}$ alkyl, $C_{1-4}$ alkoxy, $C_{1-4}$ alkoxy-$C_{1-4}$ alkoxy, phenyl-$C_{1-4}$ alkyl-oxy which may be optionally substituted by at least one substituent selected from the group consisting of halogen, $C_{1-4}$ alkyl and $C_{1-4}$ alkoxy on the phenyl nucleus, or phenyl which may be optionally substituted at least one substituent selected from the group consisting of halogen, $C_{1-4}$ alkyl and $C_{1-4}$ alkoxy on the phenyl nucleus; X is —S—, —CH=N— or —C($R^3$)=C($R^4$)—, where each of $R^3$ and $R^4$ is hydrogen, halogen, $C_{1-4}$ alkyl, $C_{1-4}$ alkoxy, $C_{1-4}$ alkoxy-$C_{1-4}$ alkoxy or phenyl-$C_{1-4}$ alkyl-oxy which may be optionally substituted by at least one substituent selected from the group consisting of halogen, $C_{1-4}$ alkyl and $C_{1-4}$ alkoxy on the phenyl nucleus; and one of A and B is oxygen, sulfur or —NH—, and the other is —C($R^5$)($R^6$)—, where each of $R^5$ and $R^6$ is hydrogen or $C_{1-4}$ alkyl.

In the present specification inclusive of each definition as mentioned above, halogen means chlorine, bromine, fluorine and iodine; $C_{1-4}$ alkyl includes methyl, ethyl, propyl, isopropyl, butyl, isobutyl or tertiary-butyl; $C_{1-4}$ alkoxy includes methoxy, ethoxy, propoxy, isopropoxy, butoxy or tertiary butoxy; $C_{1-4}$ alkoxy-$C_{1-4}$ alkoxy includes methoxymethoxy, ethoxymethoxy, propoxymethoxy, butoxymetoxy, methoxyethoxy, propoxyethoxy, butoxyethoxy, methoxypropoxy, ethoxypropoxy, propoxypropoxy, butoxypropoxy, mothoxybutoxy, ethoxybutoxy, propoxybutoxy or butoxybutoxy; phenyl-$C_{1-4}$ alkyl-oxy which may be optionally substituted by at least one substituent selected from the group consisting of halogen, $C_{1-4}$ alkyl and $C_{1-4}$ alkoxy on the phenyl nucleus includes benzyloxy, phenylethoxy, phenylpropoxy, phenylbutoxy, chlorobenzyloxy, bromobenzyloxy, methylbenzyloxy, ethylbenzyloxy, propylbenzyloxy, butylbenzyloxy, methoxybenzyloxy, ethoxybenzyloxy, propoxybenzyloxy, butoxybenzyloxy, dichlorobenzyloxy, dimethylbenzyloxy, trimethoxybenzyloxy, chlorophenylethoxy, bromophenylethoxy, methylphenylethoxy, ethylphenylethoxy, propylphenylethoxy, butylphenylethoxy, methoxyphenylethoxy, ethoxyphenylethoxy, propoxyphenylethoxy, butoxyphenylethoxy, dichlorophenylethoxy, dimethylphenylethoxy, trimethoxyphenylethoxy, chlorophenylpropoxy, methylphenylpropoxy, chlorophenylbutoxy or methylphenylbutoxy; and phenyl which may be optionally substituted by at least one substituent selected from the group consisting of halogen, $C_{1-4}$ alkyl and $C_{1-4}$ alkoxy on the phenyl nucleus includes phenyl, chlorophenyl, bromophenyl, flurophenyl, methylphenyl, ethylphenyl, propylphenyl, butylphenyl, methoxyphenyl, ethoxyphenyl, propoxyphenyl, butoxyphenyl, dichlorophenyl, dimethylphenyl or trimethoxyphenyl.

Preferable compounds of the present invention are the compounds of formula (I) wherein $R^1$ is hydrogen, halogen, $C_{1-4}$ alkyl or phenyl; $R^2$ is hydrogen, $C_{1-4}$ alkyl or phenyl; X is —S—, —CH=N— or —C($R^3$)=C($R^4$)—, where each of $R^3$ and $R^4$ is as defined above; and one of A and B is oxygen, sulfur or —NH—, and the other is —C($R^5$)($R^6$)—, where each of $R^5$ and $R^6$ is as defined above. More preferable compounds of the present invention are the compounds of formula (I) wherein $R^1$ is hydrogen or $C_{1-4}$ alkyl; $R^2$ is $C_{1-4}$ alkyl; X is —C($R^3$)=C($R^4$)—, where each of $R^3$ and $R^4$ is hydrogen; and A is oxygen; and B is —C($R^5$)($R^6$)—, where each of $R^5$ and $R^6$ is hydrogen.

The compounds of formula (I) can prepared according to one of the following methods:

METHOD 1

The compounds of formula (I) wherein A is sulfur and B is —C($R^5$)($R^6$)— can be prepared by reacting a compound of the formula:

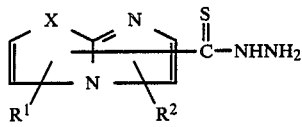
(II)

wherein each symbol is as defined above, with a compound of the formula:

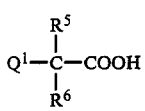
(III)

wherein $Q^1$ is halogen and $R^5$ and $R^6$ are as defined above.

The reaction is usually carried out at room temperature to a boiling point of the solvent employed for several hours to several scores of hours in a suitable solvent such as water, methanol, ethanol or dimethylformamide in the presence of an alkali hydroxide such as sodium hydroxide or potassium hydroxide or an alkali alcoholate such as sodium methylate or sodium ethylate.

METHOD 2

The compounds of formula (I) wherein A is —C(R$^5$)(R$^6$)— and A is sulfur can be prepared by reacting a compound of the formula:

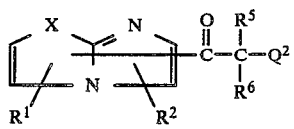   (IV)

Q$^2$ is halogen and others are as defined above, with a compound of the formula:

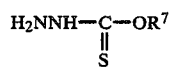   (V)

wherein R$^7$ is C$_{1-4}$ alkyl, ammonium ion or alkali metal ion (e.g. sodium or potassium).

The reaction is usually carried out at room temperature to a boiling point of the solvent employed for several hours to several scores of hours in a suitable solvent such as methanol, ethanol, propanol, acetonitrile or dimethylformamide.

METHOD 3

The compounds of formula (I) wherein A is oxygen and B is —C(R$^5$)(R$^6$)— can be prepared by subjecting a compound of the formula:

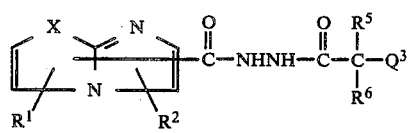   (VI)

wherein Q$^3$ is halogen and others are as defined above, to ring closure reaction.

The reaction is usually carried out at room temperature to a boiling point of the solvent employed for several hours to several scores of hours in a suitable sovent such as methanol, ethanol, acetone, methyl ethyl ketone, methyl isobutyl ketone, dimethylformamide or dimethylsulfoxide in the presence of an alkali hydroxide such as sodium hydroxide or potassium hydroxide, an alkali carbonate such as sodium carbonate or potassium carbonate, an alkali bicarbonate such as sodium bicarbonate or potassium bicarbonate, or sodium hydride.

The starting compounds of formula (VI) can be prepared by reacting a compound of the formula:

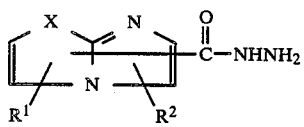   (VII)

wherein each symbol is as defined above, with a compound of the formula:

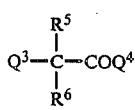   (VIII)

wherein each of Q$^3$ and Q$^4$ is halogen and others are as defined above.

METHOD 4

The compounds of formula (I) wherein A is —C(R$^5$)(R$^6$)— and B is oxygen can be prepared by subjecting a compound of the formula:

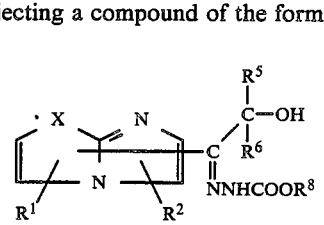   (IX)

wherein R$^8$ is C$_{1-4}$ alkyl and others are as defined above, to ring closure reaction.

The reaction is usually carried out at room temperature to a boiling point of the solvent employed for several hours to several scores of hours in a suitable sovent such as methanol, ethanol, propanol, acetone, methyl ethyl ketone, benzene, toluene or dimethylformamide in the presence of an alkali hydroxide such as sodium hydroxide or potassium hydroxide, an alkali carbonate such as sodium carbonate or potassium carbonate, an alkali bicarbonate such as sodium bicarbonate or potassium bicarbonate, an alkali alcoholate such as sodium methylate or sodium ethylate, or sodium hydride.

The starting compounds of formula (IX) can be prepared by reacting a compound of the formula:

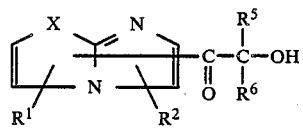   (X)

wherein each symbol is as defined above, with a compound of the formula:

   (XI)

H$_2$NNHCOOR$^8$ wherein R$^8$ is as defined above.

METHOD 5

The compounds of formula (I) wherein A is —NH— and B is —C(R$^5$)(R$^6$)— can be prepared by reacting a compound of the formula:

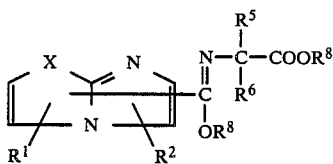   (XII)

wherein each symbol is as defined above, with hydrazine hydrate.

The reaction is usually carried out at room temperature to a boiling point of the solvent employed for several hours to several scores of hours in a suitable solvent such as methanol, ethanol, propanol, dimethylformamide, benzene or toluene.

The starting compounds of formula (XII) can be prepared by reacting a compound of the formula:

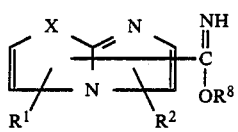

wherein each symbol is as defined above, with a compound of the formula:

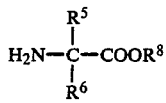

wherein each symbol is as defined above.

METHOD 6

The compounds of formula (I) wherein A is —C($R^5$)($R^6$)— and and B is —NH— can be prepared by subjecting a compound of the formula:

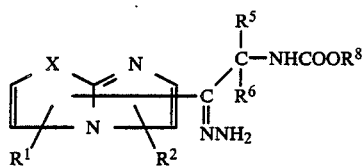

wherein each symbol is as defined above, to ring closure reaction.

The reaction is usually carried out at room temperature to a boiling point of the solvent employed for several hours to several scores of hours in a suitable solvent such as methanol, ethanol, propanol, acetonitrile or dimethylformamide.

The starting compounds of formula (XV) can be prepared by reacting a compound of the formula:

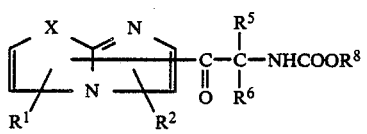

wherein each symbol is as defined above, with hydrazine hydrate.

The compounds of formula (I) thus obtained can be converted into pharmaceutically acceptable acid addition salts thereof in a conventional manner by treating with an inorganic acid such as hydrochloric acid, hydrobromic acid, sulfuric acid or phosphoric acid or an organic acid such as malonic acid, citric acid, tartaric acid, fumaric acid, succinic acid, maleic acid or methanesulfonic acid.

The following pharmacological experiments illustrate the potent effects of the compounds of the present invention.

1. Effects on platelet aggregation in vitro

[Method]

Samples of blood are collected from rats weighing 400-450 g and mixed with a 1/10 volume of 3.8% sodium citrate solution. The citrated blood is centrifugated at 200×g for 10 minutes to yield platelet-rich plasma. Test compound is added to platelet-rich plasma thus obtained and maintained at 37° C. for 2 minutes. The platelet aggregation is induced by the addition of $10^{-5}$ M adenosine diphosphate (final concentration) and measured with a Born type six channel aggregometer (Journal of Physiology, vol. 168, pp. 175-198, 1963.

50% inhibitory concentrations (IC$_{50}$, μg/ml) as compared the control group are calculated. The results are summarized in Table 1. Aspirin and ticlopidine are employed as compounds for comparison.

[Results]

TABLE 1

| Test Compound (No. of Example) | IC$_{50}$ (μg/ml) |
| --- | --- |
| 1 | 1.0 |
| 2 | 1.9 |
| 3 | 3 |
| 5 | 0.5 |
| 17 | 0.6 |
| 18 | 0.4 |
| 19 | 1.0 |
| Aspirin | >300 |
| Ticlopidine | >300 |

2. Effects on platelet aggregation ex vivo

[Method]

Test compound is orally administered to rats weighing 400-450 g. After 2 hours, samples of blood are collected from the rats and mixed with a 1/10 volume of 3.8% sodium citrate solution. The citrated blood is centrifugated at 200×g for 10 minutes to yield platelet-rich plasma. The platelet aggregation is induced by the addition of $10^{-5}$ M adenosine diphosphate (final concentration) and measured with the same aggregometer as described in the above Method.

Percentage of inhibition as compared with the control group administered with the solvent are calculated. The results are summarized in Table 2.

[Results]

TABLE 2

| Test Compound (No. of Example) | Dose (mg/kg, p.o.) | % inhibition (%) |
| --- | --- | --- |
| 1 | 10 | 75 |
| 5 | 10 | 54 |
| 16 | 10 | 60 |
| 17 | 10 | 54 |
| 18 | 10 | 65 |

The acute toxicity of the compounds of the present invention is studied in 5 male mice. The mice are observed for 5 days after the oral administration of the compound, and the mortality is calculated. All animals survive at the dose of 1000 mg/kg of the compounds of Examples 1, 2 and 3.

In view of the results of various pharmacological experiments including the above-mentioned experiments, the compounds of the present invention or pharmaceutically acceptable acid addition salts thereof are proved to exhibit potent inhibitory activity on platelet aggregation, increasing activity of blood flow, and analgesic and antiinflammatory activities. These compounds, therefore, are each useful as an active substance or ingredient of antithrombotic agents, antianginal agents, coronary circulation improving agents, cerebral circulation improving agents, peripheral circulation improving agents, analgesics and antiinflammatory agents.

The compounds of the present invention can be safely administered orally or parenterally, i.e. intraperitoneally, intraveneously or subcutaneously, in human beings in the form of a pharmaceutical composition such as tablets, sugar-coated tablets, powder, granules, pills, syrup, injectable solutions or suppositories.

The pharmaceutical composition can be prepared by, for example, mixing a therapeutically effective amount of the compound of the present invention with a conventional and pharmaceutically acceptable additives such as an excipient, an extender of a diluent. The choice of such additive is determined by the preferred form of administration the solubility of the compound and standard pharmaceutical practice.

The dose may vary depending upon the diseases to be treated or the conditions of the patients to be treated, but the daily dose for human adults preferably ranges from 10 to 1000 mg in one to several times divided doses.

| Pharmaceutical preparation: film-coated tablets containing 100 mg of active ingredient | |
|---|---|
| (a) composition of tablets | |
| Compound of Example 1 | 100.0 mg |
| Lactose | 30.0 mg |
| Corn starch | 10.0 mg |
| Polyvinyl pyrrolidone | 3.0 mg |
| Microcrystalline cellulose | 12.0 mg |
| Talc | 4.0 mg |
| Magnesium stearate | 1.0 mg |
| (b) composition of film coating agent | |
| Hydroxypropylmethycellulose | 8.5 mg |
| Polyethylene glycol 6000 | 0.5 mg |
| Talc | 1.0 mg |

A mixture of the compound of Example 1 as an active ingredient, lactose and corn starch are kneaded with an aqueous polyvinyl pyrrolidone solution and granulated through a 16 mesh sieve, and dried at 50° C. to obtain a granulate with 3-4% water content. The dry granulates are forced through a 24 mesh sieve and mixed with microcrystalline cellulose, talc and magnesium stearate. The mixture is compressed with a punch with a diameter of 7.5 mm into tablets weighing 160 mg each. The tablets thus obtained are film-coated by using hydroxypropylmethylcellulose, polyethylene glycol 6000 and talc to obtain filmcoated tablets weighing 170 mg each.

The following examples will illustrate the present invention in more detail, but they are not to be construed as limiting the present invention.

EXAMPLE 1

A mixture of 5 g of N'-chloroacetyl-2-methylimidazo[1,2-a pyridine-3-carbohydrazide and 5 g of potassium carbonate in 50 ml of dimethylformamide is stirred under heating at 70°-80° C. for 2 hours. After insoluble substances are filtered off, the filtrate is concentrated under reduced pressure and to the resulting residue is added water. Insoluble substances are collected by filtration, washed with water and recrystallized from methanol to give 1.2 g of 2-(2-methylimidazo[1,2-a]pyridin-3-yl)-4,6-dihydro-1,3,4-oxadiazin-5-one as white crystals, melting at 278°-280° C. with decomposition.

EXAMPLE 2

A mixture of 6 g of N'-chloroacetyl-2,8-dimethylimidazo[1,2-a]pyridine-3-carbohydrazide and 10 g of potassium carbonate in 50 ml of dimethylformamide is stirred under heating at 70°-90° C. for 1.5 hours. After the reaction mixture is allowed to cool, insoluble substances are collected by filtration, washed with water and recrystallized from a mixted solvent of chloroform and methanol to give 2.0 g of 2-(2,8-dimethylimidazo[1,2-a]pyridin-3-yl)-4,6-dihydro-1,3,4-oxadiazin-5-one as white crystals, melting at 310°-313° C. with decomposition.

EXAMPLE 3

A mixture of 21 g of N'-chloroacetyl-2,6-dimethylimidazo[1,2-a]pyridine-3-carbohydrazide and 30 g of potassium carbonate in 200 ml of methyl ethyl ketone and 100 ml of dimethylformamide is stirred with refluxing for 5 hours. After insoluble substances are filtered off, the solvent is distilled off and water is added to the resultant residue. The precipitated crystals are collected by filtration and recrystallized from methanol to give 3 g of 2-(2,6-dimethylimidazo[1,2-a]pyridin-3-yl)-4,6-dihydro-1,3,4-oxadiazin-5-one as white crystals, melting at 313° C. with decomposition.

Preparation of the starting compound

To a mixture of 14.8 g of 2,6-dimethylimidazo[1,2-a]pyridine-3-carbohydrazide and 7.36 g of triethylamine in 300 ml of chloroform with stirring under cooling is added dropwise a solution of 8 g of chloroacetyl chloride in 50 ml of chloroform at 5°-10° C. After the mixture is stirred for 30 minutes, the reaction temperature is raised to room temperature and the resultant mixture is further stirred for 30 minutes. To the reaction mixture is added water and the precipitated crystals are collected by filtration to give 21 g of N'-chloroacetyl-2,6-dimethylimidazo[1,2-a]pyridine-3-carbohydrazide, melting at 290°-291° C. with decomposition.

EXAMPLE 4

A mixture of 5.4 g of 3-bromoacetyl-2-methylimidazo[1,2-a]pyrimidine hydrobromide, 3 g of ethyl thiocarbazate and 100 ml of acetonitrile is stirred under reflux for 4 hours. After cooling, crystals are collected by filtration and recrystallized from methanol twice to give 2 g of 5-(2-methylimidazo[1,2-a]pyrimidin-3-yl)-3,6-dihydro-1,3,4-thiadiazin-2 -one hydrobromide as pale yellow crystals, melting at 285°-288° C. with decomposition.

EXAMPLE 5

A mixture of 16 g of N'-chloroacetyl-6-methylimidazo[2,1-b]thiazole-5-carbohydrazide and 14 g of potassium carbonate in 160 ml of dimethylformamide is stirred under heating at 50°-60° C. for 4 hours. After insoluble substances are filtered off, the dimethylformamide is distilled off and to residual oil is added ethanol. The precipitated crystals are collected by filtration and recrystallized from methanol to give 5.2 g of 2-(6-methylimidazo[2,1-b]thiazol-5-yl)-4,6-dihydro-1,3,4-oxadiazin-5-one as pale yellow crystals, melting at 274°-275° C. with decomposition.

EXAMPLE 6

To a solution of 0.5 g of metallic sodium in 60 ml of ethanol is added 6 g of hydroxymethyl-(6-methylimidazo[2,1-b]thiazol-5-yl)ketone-N-methoxycarbonylhydrazone hydrochloride, and stirred at room temperature for 3 hours. Crystals are collected by filtration, washed with water and then recrystallized from 50 ml of a mixed solvent of chloroform and methanol to give 3.5 g of 5-(6-methylimidazo[2,1-b]thiazol-5-yl)-3,6-dihydro-1,3,4-oxadiazin-2-one as white crystals, melting at 294° C. with decomposition.

Preparation of the starting compound

A mixture of 11.5 g of hydroxymethyl-(6-methylimidazo2,1-b]thiazol-5-yl)ketone,100 ml of methanol, 7 g of methoxycarbonylhydrazine and 0.5 ml of concentrated hydrochloric acid is stirred at 50° C. for an hour and the precipitated crystals are collected by filtration to give 13 g of hydroxymethyl(6-methylimidazo[2,1-b]thiazole-5-yl)ketone-N-methoxycarbonylhydrazone hydrochloride, melting at 132° C.

EXAMPLE 7

To a mixture of 32 g of imidazo[2,1-b]thiazole-5-carbothiohydrazide in 140 ml of 2 normal sodium hydroxide solution is added 52 g of bromoacetic acid portionwise under stirring. The mixture is stirred at room temperature for 10 minutes and insoluble substances are filtered off. The filtrate is further stirred at room temperature for 5 hours, and the precipitated crystals are collected by filtration and recrystallized from 300 ml of dimethylformamide to give 9 g of 2-(imidazo[2,1-b]thiazol-5-yl)-4,6-dihydro-1,3,4-thiaziadin-5-one as yellow crystals, melting at 274°–275° C. with decomposition.

EXAMPLE 8

A miture of 6.3 g of 3-chloroacetyl-2,7-dimethylimidazo[1,2-a]pyidine, 4 g of ethyl thiocarbazate, 4 g of triethylamine and 150 ml of ethanol is refluxed under stirring for 3 hours. After cooling, the ethanol is distilled off and to a solution of the residue in acetone is added a solution of hydrochloric acid in ethanol. After cooling, the precipitated crystals are collected by filtration and recrystallized from methanol to give 2 g of 5-(2,7-dimethylimidazo[1,2-a]pyridin-3-yl)-3,6-dihydro-1,3,4-thiadiazin-2-one hydrochloride as pale yellow crystals, melting at 248°–250° C. with decomposition.

EXAMPLE 9

A mixture of 7 g of 5-ethoxycarbonylaminoacetyl-6-methylimidazo[2,1-b]thiazole, 100 ml of ethanol and 8 ml of 100% hydrazine hydrate is refluxed under heating for 2 days. After cooling, crystals are collected by filtration and recrystallized from a mixed solvent of chloroform and methanol to give 3.4 g of 6-(6-methylimidazo[2,1-b]thiazol-5-yl)-4,5-dihydro-2H-1,2,4 triazin-3-one as white crystals, melting at 293°–295° C. with decomposition.

Preparation of the starting compound

To a solution of 4 g of 5-aminoacetyl-6-methylimidazo[2,1-b]thiazole hydrochloride in 50 ml of water is added a mixed solution of 3.2 g of ethyl chloroformate and 50 ml of ethyl acetate under stirring, and then 7.6 g of sodium bicarbonate is added. After the mixture is stirred at room temperature for 4 hours, chloroform and water are added to the resulting mixture. The chloroform layer is separated, washed with water and dried over magnesium sulfate, and then the chloroform is distilled off under reduced pressure. The residual oil is purified with a column chromatography using chloroform as a eluent to give 2 g of 5-ethoxycarbonylaminoacetyl-6-methylimidazo[2,1-b]thiazole.

EXAMPLE 10

A solution of 10 g of ethyl N-ethoxycarbonylmethyl-(6-methylimidazo[2,1-b]thiazol-5-yl)imidate and 10 ml of 100% hydrazine hydrate in 100 ml of ethanol is allowed to stand at room temperature for 3 days. After the ethanol is distilled off, the residue is washed with water and crystals obtained are recrystallized from a mixed solvent of chloroform and methanol to give 4.1 g of 3-(6-methylimidazo[2,1-b]thiazol-5-yl)-4,5-dihydro-1H-1,2,4-triazin-6-one as pale yellow crystals, melting at 270°–273° C. with decomposition.

Preparation of the starting compound

A mixture of 8 g of ethyl (6-methylimidazo[2,1-b]thiazol-5-yl)iminoether and 8 g of ethyl glycinate hydrochloride in 100 ml of ethanol is allowed to stand at room temperature for 3 days, and then the ethanol is distilled off. After the resultant mixture is extracted with chloroform, the extract is washed with water and dried over magnesium sulfate, and then the chloroform is distilled off under reduced pressure to give 3 g of ethyl N-ethoxycarbonylmethyl-(6-methylimidazo[2,1-b]thiazol-5-yl)imidate.

The following compounds can be prepared in a similar manner as mentioned above:
(11) 2-(2,7-Dimethylimidazo[1,2-a]pyridin-3-yl)-4,6-dihydro-1,3,4-oxadiazin-5-one hydrochloride, melting at 260°–262° C. with decomposition
(12) 2-(6-Bromo-2-methylimidazo[1,2-a]pyridin-3-yl)-4,6-dihydro-1,3,4-oxadiazin-5-one hydrochloride, melting at 283°–285° C. with decomposition
(13) 2-(3-Methyl-6-phenylimidazo[2,1-b]thiazol-5-yl)-4,6-dihydro-1,3,4-oxadiazin-5-one, melting at 308°–310° C. with decomposition
(14) 2-(3-Phenylimidazo[2,1-b]thiazol-2-yl)-4,6-dihydro-1,3,4-oxadiazin-5-one, melting at 214°–217° C. with decomposition
(15) 2-(2-Phenylimidazo[1,2-a]pyridin-3-yl)-4,6-dihydro-1,3,4-oxadiazin-5-one, melting at 227°–231° C. with decomposition
(16) 2-(Imidazo[2,1-b]thiazol-3-yl)-4,6-dihydro-1,3,4-oxadiazin-5-one, melting at 287°–288° C. with decomposition
(17) 2-(3-Methylimidazo[2,1-b]thiazol-2-yl)-4,6-dihydro-1,3,4-oxadiazin-5-one, melting at 256°–257° C. with decomposition
(18) 2-(Imidazo[1,2-a]pyridin-6-yl)-4,6-dihydro-1,3,4-oxadiazin-5-one, melting at 279°–281° C. with decomposition
(19) 2-(Imidazo[1,2-a]pyridin-8-yl)-4,6-dihydro-1,3,4-oxadiazin-5-one hydrochloride, melting at 340° C. with decomposition
(20) 5-(6-Methylimidazo[2,1-b]thiazol-5-yl)-3,6-dihydro-1,3,4-thiadiazin-5-one, melting at 282° C. with decomposition
(21) 5-(2-Phenylimidazo[1,2-a]pyridin-3-yl)-3,6-dihydro-1,3,4-oxadiazin-2-one, melting at 280°–282° C. with decomposition
(22) 5-(2-Methylimidazo[1,2-a]pyridin-3-yl)-3,6-dihydro-1,3,4-oxadiadin-2-one, melting at 260°–263° C. with decomposition
(23) 2-(8-Benzyloxy-2-methylimidazo[1,2-a]pyridin-3-yl)-4,6-dihydro-1,3,4-oxadiazin-5-one, melting at 245°–247° C.
(24) 2-(8-Methoxy-2-methylimidazo[1,2-a]pyridin-3-yl)-4,6-dihydro-1,3,4-oxadiazin-5-one, melting at 229°–230° C.
(25) 2-(8-Ethoxymethoxy-2-methylimidazo[1,2-a]pyridin-3-yl)-4,6-dihydro-1,3,4-oxadiazin-5-one, melting at 163°–164° C.

(26) 2-(2,5-Dimethylimidazo[1,2-a]pyridin-3-yl)-4,6-dihydro-1,3,4-oxadiazin-5-one, melting at 234°-236° C.

(27) 2-(6-Chloro-2-methylimidazo[1,2-a]pyridin-3-yl)-4,6-dihydro-1,3,4-oxadiazin-5-one, melting at 312°-315° C. with decomposition

(28) 2-(8-Bromo-2-methylimidazo[1,2-a]pyridin-3-yl)-4,6-dihydro-1,3,4-oxadiazin-5-one

(29) 2-(8-(4-Chlorobenzyloxy)-2-methylimidazo[1,2-a]pyridin-3-yl)-4,6-dihydro-1,3,4-oxadiazin-5-one

(30) 2-(8-Ethyl-2-methylimidazo[1,2-a]pyridin-3-yl)-4,6-dihydro-1,3,4-oxadiazin-5-one

(31) 2-(8-Isopropyl-2-methylimidazo[1,2-a]pyridin-3-yl)-4,6-dihydro-1,3,4-oxadiazin-5-one

(32) 2-(8-(4-Methylbenzyloxy)-2-methylimidazo[1,2-a]pyridin-3-yl)-4,6-dihydro-1,3,4-oxadiazin-5-one

(33) 5-(2-Methylimidazo[1,2-a]pyrimidin-3-yl)-4,6-dihydro-1,3,4-oxadiazin-5-one

(34) 2-(8-(4-Methoxybenzyloxy)-2-methylimidazo[1,2-a]pyridin-3-yl)-4,6-dihydro-1,3,4-oxadiazin-5-one

(35) 2-(2-(4-Chlorophenyl)imidazo[1,2-a]pyridin-3-yl)-4,6-dihydro-1,3,4-oxadiazin-5-one

(36) 2-(2-(4-Methylphenyl)imidazo[1,2-a]pyridin-3-yl)-4,6-dihydro-1,3,4-oxadiazin-5-one

(37) 2-(2-(4-Methoxyphenyl)imidazo[1,2-a]pyridin-3-yl)-4,6-dihydro-1,3,4-oxadiazin-5-one Although the present invention has been adequately discussed in the foregoing specification and examples included therein, one readily recognizes that various changes and modifications may be made without departing from the spirit and scope thereof.

What is claimed is:

1. An oxodiazine compound of the formula:

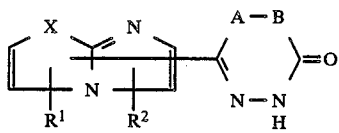

or a pharmaceutically acceptable acid addition salt thereof, wherein each of $R^1$ and $R^2$ is hydrogen, halogen, $C_{1-4}$ alkyl, $C_{1-4}$ alkoxy, $C_{1-4}$ alkoxy-$C_{1-4}$ alkoxy, phenyl-$C_{1-4}$ alkyl-oxy which may be optionally substituted by at least one substituent selected from the group consisting of halogen, $C_{1-4}$ alkyl and $C_{1-4}$ alkoxy on the phenyl nucleus, or phenyl which may be substituted by at least one substituent selected from the group consisting of halogen, $C_{1-4}$ alkyl and $C_{1-4}$ alkoxy on the phenyl nucleus; X is —S—, —CH=N— or —C($R^3$)=C($R^4$)—, where each of $R^3$ and $R^4$ is hydrogen, halogen, $C_{1-4}$ alkyl, $C_{1-4}$ alkoxy, $C_{1-4}$ alkoxy-$C_{1-4}$ alkoxy or phenyl-$C_{1-4}$ alkyl-oxy which may be optionally substituted by at least one substituent selected from the group consisting of halogen, $C_{1-4}$ alkyl and $C_{1-4}$ alkoxy on the phenyl nucleus; and one of A and B is oxygen or sulfur and the other is —C($R^5$)($R^6$)—, where each of $R^5$ and $R^6$ is hydrogen or $C_{1-4}$ alkyl.

2. The compounds of claim 1 wherein $R^1$ is hydrogen, halogen, $C_{1-4}$ alkyl or phenyl; $R^2$ is hydrogen, $C_{1-4}$ alkyl or phenyl; X is —S—, —CH=N— or —C($R^3$)=C($R^4$)—, where each of $R^3$ and $R^4$ is hydrogen, $C_{1-4}$ alkyl, $C_{1-4}$ alkoxy, $C_{1-4}$ alkoxy-$C_{1-4}$ alkoxy or phenyl-$C_{1-4}$ alkyl-oxy which may be optionally substituted by at least one substituent selected from the group consisting of halogen, $C_{1-4}$ alkyl and $C_{1-4}$ alkoxy on the phenyl nucleus; and one of A and B is oxygen or sulfur and the other is —C($R^5$)($R^6$)—, where each of $R^5$ and $R^6$ is hydrogen or $C_{1-4}$ alkyl.

3. The compounds of claim 1 wherein $R^1$ is hydrogen or $C_{1-4}$ alkyl; $R^2$ is $C_{1-4}$ alkyl; X is —C($R^3$)=C($R^4$)—, where each of $R^3$ and $R^4$ is hydrogen; A is oxygen; and B is —C($R^5$)($R^6$)—, where each of $R^5$ and $R^6$ is hydrogen.

4. The compound of claim 1: 2-(2-methylimidazo[1,2-a]pyridin-3-yl)-4,6-dihydro-1,3,4-oxadiazin-5-one.

5. The compound of claim 1: 2-(2,8-dimethylimidazo[1,2-a]pyridin-3-yl)-4,6-dihydro-1,3,4-oxadiazin-5-one.

6. The compound of claim 1: 2-(2,6-dimethylimidazo[1,2-a]pyridin-3-yl)-4,6-dihydro-1,3,4-oxadiazin-5-one.

7. A pharmaceutical composition comprising a compound of claim 1 in a therapeutically effective amount sufficient to inhibit platelet aggregation, increase blood flow, or act as an analgesic or anti-inflammatory agent with pharmaceutically acceptable additives.

* * * * *